United States Patent [19]

Laurence

[11] Patent Number: 5,171,841
[45] Date of Patent: Dec. 15, 1992

[54] T-CELL SUPPRESSOR PROTEIN

[75] Inventor: Jeffrey C. Laurence, Larchmont, N.Y.

[73] Assignee: Cornell Research Foundation, Inc., Ithaca, N.Y.

[21] Appl. No.: 506,480

[22] Filed: Apr. 9, 1990

[51] Int. Cl.⁵ .............................................. A61K 13/00
[52] U.S. Cl. ................................... 530/350; 530/351; 435/69.1
[58] Field of Search ................ 530/350, 351; 435/69.1

[56] References Cited

U.S. PATENT DOCUMENTS 4,665,032  5/1987  Laurence ........................... 435/240

OTHER PUBLICATIONS

Aune et al., Proc. Natl. Acad. Sci. USA, 78(8) 5099–5103 (1981).
"Soluble Immunosuppressor Factors in Human Cancer", Guidi et al., Clinical Immunology Newsletter, 124–127 (9:8 1988).
"The Immune System in AIDS", Laurence, Scientific American, vol. 253, pp. 84–93, (Dec. 1985).
"Immunoregulatory Lymphokines of T Hybridomas from AIDS Patients: Constitutive and Inducible Suppressor Factors", Laurence et al., Science, vol. 225, pp. 66–69, (Jul. 6, 1984).
"DNA Cloning, vol. I, a practical approach", Glover, ed., IRL Press, Oxford/Washington, D.C. (1985).
"Soluble Suppressor Factors in Patients with Acquired Immune Deficiency Syndrome and Its Prodrome", Journal of Clinical Investigation, vol. 72, pp. 2072–2081 (Dec. 1983).
"Establishment of a human T-cell hybrid line with suppressive activity", Grillot-Courvalin et al., Nature, vol. 292, pp. 844–845 (Aug. 27, 1981).

Primary Examiner—David L. Lacey
Assistant Examiner—Shelly J. Guest
Attorney, Agent, or Firm—Testa, Hurwitz & Thibeault

[57] ABSTRACT

The invention provides a purified protein substantially free of other human proteins, having an amino acid sequence sufficiently duplicative of the sequence:

TyrThrAsnHisAlaGlyGluLeuValArgGlyAspGlnArgIleTrpMetAla
GlnLeuLysAspGlyValProPheThrAlaGlyAlaPheThrThrGlyLysThr
ProPheMetMetPheGlyLeuProAlaAlaAlaPheAlaIleTyrLysAsnAla
ArgProGluArgLysLysValValGlyGlyLeuMetLeuSerAlaGlyLeuThr
AlaPheLeuThrGlyIleThrGluProLeuGluPheSerPheLeuPheValAla
ProVal such that the protein is capable of selectively suppressing the immune function of T-helper cells.

2 Claims, 2 Drawing Sheets

```
         10           20            30          40
     TyrThrAsnHisAlaGlyGluLeuValArgGlyAspGlnArgIleTrp
     GGAAGTTATACAAATCACGCAGGTGAATTAGTTCGTGGTGACCAACGTATTTGG 50           60           70           80           90          100
     MetAlaGlnLeuLysAspGlyValProPheThrAlaGlyAlaPheThrThrGly
     ATGGCACAATTGAAAGATGGCGTACCATTTACTCCTGGTGCATTTACTACTGGT 110          120          130          140          150
     LysTyrProPheMetMetPheGlyLeuProAlaAlaAlaPheAlaIleTyrLys
     AAATATCCATTCATGATGTTTGGTTTACCAGCGGCAGCATTTGCGATTTATAAA 160          170          180          190          200          210
     AsnAlaArgProGluArgLysLysValValGlyGlyLeuMetLeuSerAlaGly
     AATGCACGACCAGAACGTAAAAAAGTTGTTGGTGGTTTAATGTTATCAGCAGGA 220          230          240          250          260
     LeuThrAlaPheLeuThrGlyIleThrGluProLeuGluPheSerPheLeuPhe
     TTAACTGCATTTTTAACTGGTATCACTGAGCCATTAGAATTTTCATTCTTATTT 280          290
     ValAlaProVal
     GTAGCACCAGTACTCTAT
```

```
             10          20         30         40
      TyrThrAsnHisAlaGlyGluLeuValArgGlyAspGlnArgIleTrp
GGAAGTTATACAAATCACGCAGGTGAATTAGTTCGTGGTGACCAACGTATTTGG 50         60         70         80         90        100
MetAlaGlnLeuLysAspGlyValProPheThrAlaGlyAlaPheThrThrGly
ATGGCACAATTGAAAGATGGCGTACCATTTACTCCTGGTGCATTTACTACTGGT 110        120        130        140        150
LysTyrProPheMetMetPheGlyLeuProAlaAlaAlaPheAlaIleTyrLys
AAATATCCATTCATGATGTTTGGTTTACCAGCGGCAGCATTTGCGATTTATAAA 160        170        180        190        200        210
AsnAlaArgProGluArgLysLysValValGlyGlyLeuMetLeuSerAlaGly
AATGCACGACCAGAACGTAAAAAAGTTGTTGGTGGTTTAATGTTATCAGCAGGA 220        230        240        250        260
LeuThrAlaPheLeuThrGlyIleThrGluProLeuGluPheSerPheLeuPhe
TTAACTGCATTTTTAACTGGTATCACTGAGCCATTAGAATTTTCATTCTTATTT 280        290
ValAlaProVal
GTAGCACCAGTACTCTAT
```

FIG. 1

T-CELL SUPPRESSOR PROTEIN

This invention was made, at least in part, using NIH research contract funding. The Federal Government has certain rights in this invention.

BACKGROUND OF THE INVENTION

This invention relates to proteins characterized by the ability to selectively inhibit T-cell mediated immune responses.

U.S. Pat. No. 4,665,032 issued May 12, 1987 and an article by Laurence et al Immunoreoulatory Lymohokines of T-Hybridomas from AIDS Patients: Constitutive and Inducible Suppressor Factors (Science, 6th, Jul., 1984, Vol. 225, pgs. 66–69) together disclose the existence of an immune response suppressor activity originally discovered in lectin-free cultures of peripheral blood mononuclear cells from AIDS patients. The patent discloses the preparation of T-cell hybridoma cell lines which can be cultured as a source of the active protein called "soluble suppressor factor" or SSF. The putative protein differs significantly in its physiological effects from various other materials classed as soluble suppressor factors (see, e.g., Soluble Immunosuppressor Factors in Human Cancer, Guidi et al., Clinical Immunology Newsletter 9:8, 1988, pg. 124) in that it selectively inhibits T-cell dependent immune responses. A pharmaceutical grade source of this new SSF would be useful in the management of disorders requiring immunosuppression such as autoimmune diseases, hypersensitivity reactions, and organ allografting procedures. However, despite the availability of continuous cell lines which secrete the suppressor factor, and therefore necessarily contains messenger RNA encoding it, determination of the primary structure of the protein has eluded the art.

It is an object of the invention to provide soluble suppressor factors, including native form materials, muteins, truncated analogs, fusion proteins, and other constructs, capable of specifically inhibiting T-cell immune responses in humans and other mammals. Another object is to provide DNA encoding the active region of a protein capable of inhibiting selectively human T-cell immune responses.

SUMMARY OF THE INVENTION

DNA sequence data has now been derived from a λgtll subtractive hybridization library produced by cross-hybridizing single stranded cDNA from a pair of T-cell hybridomas, one of which is positive for the SSF suppression and one of which is negative. The reading frame of the DNA has been determined, and it has been expressed in E. coli to produce fusion proteins which display selective suppression of T-cell mediated immune response. The amino acid sequence encoded by this DNA thus comprises a portion of the human protein responsible for the selective immune suppressing activity previously observed in cultures of peripheral blood mononuclear cells obtained from AIDS patients and in cultures of the T-cell hybridomas disclosed in U.S. Pat. No. 4,665,032. Contrary to previous speculation, the suppressor factor is a protein encoded by the human genome whose expression presumably is stimulated during the course of a Human Immunodeficiency Virus (HIV) infection.

The invention provides a family of proteins produced by expression in a host cell of recombinant DNA, the DNA itself, and host cells harboring and capable of expressing the DNA. The DNA retrieved from the hybridoma has the sequence:

```
              10         20         30         40         50
    TATACAAATCACGCAGGTGAATTAGTTCGTGGTGACCAACGTATTTGGATGGCA 60         70         80         90        100         1
    CAATTGAAAGATGGCGTACCATTTACTCCTGGTGCATTTACTACTGGTAAATAT 10        120        130        140        150        160
    CCATTCATGATGTTTGGTTTACCAGCGGCAGCATTTGCGATTTATAAAAATGCA 170        180        190        200        210
    CGACCAGAACGTAAAAAAGTTGTTGGTGGTTTAATGTTATCAGCAGGATTAACT 220        230        240        250        260        270
    GCATTTTTAACTGGTATCACTGAGCCATTAGAATTTTCATTCTTATTTGTAGCA

CCAGTA
```

The proteins comprise an amino acid sequence sufficiently duplicative of the sequence:

TyrThrAsnHisAlaGlyGluLeuValArgGlyAspGlnArgIleTrpMetAla
GlnLeuLysAspGlyValProPheThrAlaGlyAlaPheThrThrGlyLysThr
ProPheMetMetPheGlyLeuProAlaAlaAlaPheAlaIleTyrLysAsnAla
ArgProGluArgLysLysValValGlyGlyLeuMetLeuSerAlaGlyLeuThr
AlaPheLeuThrGlyIleThrGluProLeuGluPheSerPheLeuPheValAla
ProVal such that it is capable of selectively suppressing the immune function of T-helper cells. This sequence was inferred from the retrieved DNA. The native form protein is a single polypeptide chain having an apparent molecular weight of about 57 thousand daltons as measured by comparison with molecular weight standards in polyacrylamide gel electrophoresis. Protein constructs of the invention are characterized by the ability to suppress T-cell immune response, as demonstrated, for example, by the following properties: a) inhibit proliferation of T-cells stimulated by alloantigen as well as anti CD4 monoclonal antibody; b) inhibit phytohemagglutinin-induced T-cell blastogenesis; c) inhibit poke weed mitogen-induced T-cell blastogenesis; d) inhibit poke weed mitogen-induced immunoglobulin synthesis; e) inhibit interleukin-2-dependent T-cell proliferation and f) cross react with anti-transmembrane envelope protein p15E antibody which recognizes a mammalian retrovirus associated protein. For protocols of assays for the foregoing, see infra and U.S. Pat. No. 4,665,032 and the references cited therein.

In another aspect, the invention provides a labelled probe for isolating from a cDNA or genomic library the full length nucleotide sequence (or fragments thereof) encoding the amino acid sequence of native form human and other mammalian SSF protein. The probe comprises a portion of the DNA sequence set forth above suitably labelled using conventional techniques. Using the probe, one can elucidate the full length DNA sequence and amino acid sequence of human soluble suppressor factor. This work currently is in progress. However, the invention is not limited to the native form mature protein, but further provides muteins (i.e., amino acid sequences having amino acid substitutions in one or more positions of the native form protein), deletion mutants, addition mutants, truncated analogs, fusion proteins, and other constructs comprising a sequence sufficiently duplicative of the amino acid sequence set forth above such that the protein is characterized by the ability to suppress selectively T-helper cell immune response.

BRIEF DESCRIPTION OF THE DRAWING

FIG. 1 is a 0.28 kb DNA and the amino acid sequence it encodes comprising a portion of the DNA and amino acid sequence of native form human T-cell immunosuppressive factor. The six 3' and 5' residues constitute EcoRI splice sites and are not part of the SSF sequence;

DESCRIPTION

Figure 2:
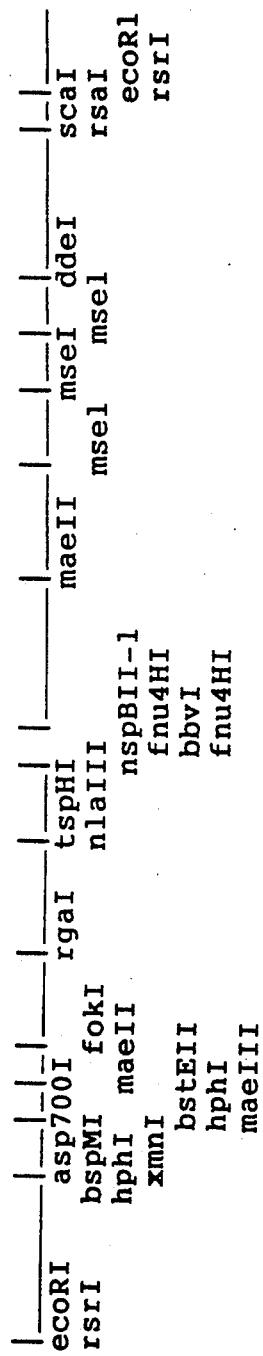
FIG. 2 is a restriction map of the DNA of FIG. 1.

In an attempt to obtain sequence information for SSF, the DNA from T-cell hybridoma SK7 (ATCC No. HB8584, 12301 Parklawn Drive, Rockville, MD 20852 deposited prior to the filing of this application) which expresses SSF was cross-hybridized with DNA from an SSF negative hybridoma designated SK23 made in accordance with the procedure set forth in U.S. Pat. No. 4,665,032, the disclosure of which is incorporated herein by reference. The DNA from SK7 which failed to hybridize was used to produce a subtractive library using the λgt11 phage expression vector. mRNA corresponding to the human DNAs in the library was then made using RNA polymerase, and the mRNA mixture was tested for expression in the rabbit reticulocyte lysate transient expression system. SSF activity was found in the supernatant as measured by suppression of T-cell proliferation in response to stimulation by mitogen using the procedure disclosed in the above-referenced patent. Attempts were then made to probe the λgt11 subtractive library by assaying for the presence of SSF expressed in the various clones. To that end, partially purified samples of SSF from hybridoma SK7 and partially purified protein produced in the rabbit reticulocyte expression system were used to immunize mice in an attempt to produce monoclonal antibodies or polyclonal antisera. However, no antibodies were produced, presumably because the presence of SSF blocked the required immune response.

It was observed that immune suppression frequently accompanies retroviral infection, that SSF was produced after infection with the HIV retrovirus, and that the transmembrane envelope protein p15E had been implicated in the pathogenesis of retroviral infections. In addition, conversation of amino acids has been noted among analogous regions of murine leukemia virus, feline leukemia virus, gibbon leukemia virus, endogenous human retroviral clones, human T-cell lymphotropic virus types I and II (HTLV-I, II), and HIV. These observations suggested the possibility that antibody to p15E may cross-react with SSF.

Thus, antimurne leukemia virus p15E monoclonal antiboides an dpolyclonal anti-p15E antisera were used to define potential relationships between SSF and p15E. Peripheral blood mononuclear cells sampled from two HIV sero-negative donors were activated with phytohemagglutinin and infected with HIV. Cells were metabolitically labeled with 35S methionine and cysteine, lysed, and precipitated with rabbit anti-p15E antiserum. A band of 57,000 daltons was observed by PAGE in the infected cell lysates but not in the controls.

The radioimmunoprecipitation studies then were repeated using SK7, which constitutively secretes SSF but does not express HIV specific proteins, as determined by indirect membrane immunofluorescence and radioimmunoprecipitation with anti-HIV reagents. SK7 also does not contain HIV specific proviral DNA, as determined by southern blotting using a complete HIV-1 probe. Nevertheless, the anti-p15E serum again detected the 57 kd band, which was absent in the mutagenized fusion partner of SK7 and in the SSF negative SK23 T-cell hybridoma. The band appeared to represent a single polypeptide as no alteration of mobility was seen when the gels were run under reducing and non-reducing conditions. The bomility of the protein appeared unaffected by glycosylase digestion, suggesting that the protein is not glycosylated. Additional experiments indicated the 57 k band might contain the SSF activity, although attempts to assay for activity of protein sliced from the gel were inconclusive. It then was decided to attempt to probe the expression products of the λgt11 library using the p15E monoclonal antibody.

The work resulted in retrieval of several DNA sequences having overlapping homoglogous regions which defined an open reading frame. The DNA sequence and the amino acid sequence it encodes is set forth in FIG. 1. A restriction map of the sequence is set forth in FIG. 2. Computerized DNA databank searching suggested the sequence had never before been reported. The DNA was then expressed in E. coli as a β-galactosidase fusion protein. Subsequent assay as described below based on inhibition of peripheral blood mononuclear cell proliferation after stimulation with poke weed mitogen indicated that the recombinant fusion protein selectively suppressed the immune function of T-helper cells, indicating that it comprises an active portion of the native amino acid sequence of SSF. Purified plasmid DNA (pIBI 30, 31) containing the SSF DNA set forth in FIG. 1 was deposited with the American Type Culture Collection (ATCC), Rockville, MD. on Dec. 12, 1990, under the provisions of the Budapest Treaty and assigned ATCC accession number 40932.

HOW TO MAKE

Knowledge of the SSF sequence as disclosed herein will enable skilled molecular biologists and genetic engineers to produce large quantities of SSF and derivative proteins for therapeutic and in vitro use. The artisan can synthesize SSF or active analogs thereof using conventional chemical solid or solution phase peptide synthesize techniques. Also, knowledge of the sequence permits expression of SSF or active analogs in various types of host cells, including both procaryotes and eucaryotes, to produce large quantities of the protein, or active analogs, and other constructs capable of selectively suppressing T-helper cell activity in mammals.

The activity of a particular construct can be assayed readily following the procedure disclosed in U.S. Pat. No. 4,665,032.

The recombinant DNA techniques exploited in this procedure are well known and do not per se form a part of this invention. Briefly, a gene encoding the amino acid sequence, or various analogs thereof, can be produced, for example, by oligonucleotide synthesis and subsequent ligation if necessary to form a complete coding region. Alternatively, all or a portion of the DNA sequence set forth in FIG. 1 or its complement may be labeled using conventional techniques and used to probe cDNA or genomic libraries to obtain additional sequence information. region may be ligated to 3' and 5' untranslated DNA regions constituting a poly A site, promoter, ribosome binding site, stop and start codons, etc. Fused DNAs can be produced for expression in procaryotes. The construction of an expression vector suitable for transfection in a selected cell type also is within the skill of the art. Culture of transformed cells results in intracellular accumulation or secretion of protein which may be purified, refolded, and otherwise post-translationally modified as desired or as necessary using conventional techniques.

HOW TO USE

The compounds produced as set forth above can be formulated into pharmaceutical preparations for therapeutic use. In particular, SSF constructs will have clinical efficacy including preparation for organ and tissue allotransplantation, treatment of aggressive autoimmune disorders, treatment of severe hypersensitivity reactions, and other diseased states wherein suppression of T-cell function has clinical utility. For example, SSF may be useful in the treatment of rheumatoid arthritis, systemic lupus erythematosus, juvenile onset insulin dependent diabetes mellitus, graft versus host disease, and inflammatory bowel disease. Another potential utility would be as an antiproliferative agent in the therapy of, e.g., T-cell cancers. These constructs can be administered to mammalian hosts for veterinary use such as with domestic animals, and for clinical use in humans in a manner similar to other therapeutic agents. The constructs can be used in an amount per administration which may vary depending on the severity of the condition treated until benefits have been obtained. These compounds can be administered neat, as mixtures with other pharmacologically active or inactive materials, or with physiologically suitable carriers such as, e.g., water, normal saline, or buffers compatible with physiological conditions. If ingested through the digestive system, the proteins are ineffective unless protected from the effects of digestive proteases. Injection can be subcutaneous, intravenous, or intramuscular. These compounds may be administered as pharmacologically acceptable salt such as acid addition salts. The proteins may be stored in lyophilized form and reconstituted just prior to use. The SSF constructs also may be used in vitro to modulate T-cell activity in transient or continuous mammalian cell cultures.

The invention will be further understood from the following non-limiting example.

The DNA of FIG. 1 was expressed as a $\beta$ galactosidase fusion protein in accordance with the method of DM Glover (*DNA Cloning*. Vol. 1, IRL Press, Oxford, 1985, pp. 76–77). The λgtll viral vector harboring the SK7 insert was introduced into the commercially available Y1089 strain of *E. coli*. Y1089 contains:

(i) the lac repressor (lacI gene product), which prevents lacZ-directed gene expression until depressed by the addition of isopropalthio galactoside (IPTG) to the medium;

(ii) a deficiency in the lon protease, which increases the stability of the recombinant fusion protein; and (iii) a mutation which enhances the frequency of phage lysogeny (hflA150).

To produce the recombinant fusion protein, Y1089 was lysogenised with the λgtll clone of interest. The lysogen was grown to high cell density, lacZ-directed fusion protein production was induced by the addition of IPTG to the medium, and the cells were harvested and lysed. More specifically, the following protocol was employed:

(i) Grow Y1089 cells in LB medium (pH 7.5)/0.2% maltose at 37° C. to saturation.

(ii) Infect the Y1089 cells with the λgtll recombinant phage at a multiplicity of approximately 5 for 20 min at 32° C. in LB medium (pH 7.5) supplemented with 10 mM MgCl$_2$.

(iii) Plate the cells on LB plate (pH 7.5) at a density of approximately 200 per plate and incubate at 32° C. (At this temperature, the temperature-sensitive phage repressor is functional.)

(iv) Test single colonies for temperature sensitivity at 42° C. Spot cells from single colonies using sterile toothpicks onto two LB plates (pH 7.5). Incubate the first plate at 42° C. and the second at 32° C.

(v) Clones which grow at 32° C. but not at 42° C. are assumed to be lysogens. Lysogens arise at a frequency between 10% and 70%.

Crude lysate was prepared as follows:

(i) Inoculate 100 ml of LB medium (pH 7.5) with a single colony of the Y1089 recombinant lysogen. Incubate the culture at 32° C. with good aeration.

(ii) When the culture has grown to an optical density of 0.5 measured at 600 nm, inCreaSe the temperature of the culture to 42-45° C. as rapidly as possible, and incubate the culture at the elevated temperature for 20 min with good aeration.

(iii) Add IPTG to 10 mM.

(iv) Incubate the culture at 37-38° C. for approximately 60 min. (Do not let the temperature of the culture drop below 37° C.) At this stage, the Y1089 lysogen will sometimes lyse, even though Y1089 does not suppress the mutation causing defective lysis (S100) in λgtll. This is a consequence firstly of the "leakiness" of the S100 amber mutation and secondly because the accumulation of foreign proteins in *E. coli* often renders it susceptible to lysis. For this reason, the longest incubation time achievable at 37-38° C. without lysis occurring should be determined for an individual recombinant lysogen.

(v) Harvest the cells as rapidly as possible in, for example, a Beckman JA-10 rotor at 5000 r.p.m. for 5 min at 24-37° C. (A sudden shift in temperature during harvest appears to increase the rate of proteolysis in experiments done on a small number of different lysogens. Therefore, centrifugation is done at a temperature between 24 and 37° C.)

(vi) Rapidly resuspend the cells in 1/20 to 1/50 of the original culture volume in a buffer suitable for proteins.

(vii) Immediately freeze the resuspended cells in liquid nitrogen.

(viii) Thaw the frozen cells to result in essentially complete lysis of the induced lysogen.

The crude lysate was dissolved in Tris-EDTA buffer containing 1 nM PMSF (protease inhibitor), and purified on an anti-$\beta$-galactosidase affinity column purchased from Promega, Inc. (Protosorb-Lac Z column) in accordance with the manufacturers instructions.

The activity of the β-gal fusion protein contained in the eluate was assayed in accordance with the methods disclosed in J. Clin. Invest. 72, 2072, 1983, Laurence J. et al. The assay involves measurement of proliferation of poke weed mitogen activated peripheral blood mononuclear cell as assessed by the incorporation of tritiated thymidine. The results are set forth in the table below.

EFFECT OF CLONE 9-B-gal FUSION PROTEIN ON PWM-DRIVEN PBMC PROLIFERATION

| SAMPLE | PEPTIDE | (CONC) (v/v) | $^3$H-Thymidine Incorporation (Counts) | PERCENT INHIBITION |
|---|---|---|---|---|
| 1 | — | — | 6104 | — |
| 2 | Buffer | 2.5% | 6667 | 0 |
|  | " | 15% | 6979 | 0 |
|  | " | 30% | 6390 | 0 |
| 3 | β-gal fusion | 2.5 | 5924 | 3.0 |
|  | " | 15% | 5551 | 9.1 |
|  | " | 30% | 3058 | 49.9 |
| 4 | β-gal fusion | 2.5 | 6692 | 0 |
|  | " | 15% | 4966 | 18.6 |
|  | " | 30% | 2142 | 64.9 |
| 5 | Control* | 2.5 | 6949 | 0 |
|  | " | 15% | 5611 | 8.1 |
|  | " | 30% | 5890 | 3.5 |
| 6 | Control* | 2.5 | 6458 | 0 |
|  | " | 15% | 4946 | 19.0 |
|  | " | 30% | 5661 | 7.3 |

*effluent collected during column loading

As is apparent from foregoing data, the recombinant fusion protein comprising β-gal and the SSF construct reproducibly and in a dose dependent manner is capable of inhibiting proliferation of activated PBM cells, a property of the native form human SSF.

The invention may be embodied in other specific forms without departing from the spirit and essential characteristics thereof. Accordingly, other embodiments are within the following claims.

What is claimed is:

1. A purified protein substantially free of other human proteins, said protein comprising an amino acid sequence sufficiently duplicative of the sequence:

TyrThrAsnHisAlaGlyGluLeuValArgGlyAspGlnArgIleTrpMetAla
GlnLeuLysAspGlyValProPheThrAlaGlyAlaPheThrThrGlyLysThr
ProPheMetMetPheGlyLeuProAlaAlaAlaPheAlaIleTyrLysAsnAla
ArgProGluArgLysLysValValGlyGlyLeuMetLeuSerAlaGlyLeuThr
AlaPheLeuThrGlyIleThrGluProLeuGluPheSerPheLeuPheValAla
ProVal such that said protein is capable of selectively suppressing the immune function of human T-helper cells.

2. The purified protein of claim 1, comprising a single polypeptide chain having a molecular weight of 57,000 daltons as measured by comparison to molecular weight standards in polyacrylamide gel electrophoresis.

* * * * *